US011730749B2

(12) United States Patent
Roman et al.

(10) Patent No.: US 11,730,749 B2
(45) Date of Patent: Aug. 22, 2023

(54) COMPOSITIONS AND METHODS FOR IMPROVING GUT HEALTH

(71) Applicant: Plexus Worldwide, LLC., Scottsdale, AZ (US)

(72) Inventors: Stephen Roman, Chandler, AZ (US); Tianan Jiang, Scottsdale, AZ (US); Marco Rebaza, Gilbert, AZ (US)

(73) Assignee: Plexus Worldwide, LLC, Scottsdale, AZ (US)

( * ) Notice: Subject to any disclaimer, the term of this patent is extended or adjusted under 35 U.S.C. 154(b) by 156 days.

(21) Appl. No.: 15/973,501

(22) Filed: May 7, 2018

(65) Prior Publication Data
US 2018/0318323 A1 Nov. 8, 2018

Related U.S. Application Data

(60) Provisional application No. 62/502,571, filed on May 5, 2017, provisional application No. 62/513,135, filed on May 31, 2017.

(51) Int. Cl.
*A61K 31/702* (2006.01)
*A61K 36/74* (2006.01)
*A61K 36/605* (2006.01)
*A61K 36/38* (2006.01)
*A61K 31/385* (2006.01)
*A61K 31/216* (2006.01)

(52) U.S. Cl.
CPC .......... *A61K 31/702* (2013.01); *A61K 31/216* (2013.01); *A61K 31/385* (2013.01); *A61K 36/38* (2013.01); *A61K 36/605* (2013.01); *A61K 36/74* (2013.01)

(58) Field of Classification Search
None
See application file for complete search history.

(56) References Cited

U.S. PATENT DOCUMENTS

2008/0102131 A1* 5/2008 Nagira .................. A61K 31/355
424/489
2012/0034323 A1* 2/2012 Doherty ............... A61K 36/889
424/727

FOREIGN PATENT DOCUMENTS

CN 106107295 A * 11/2016

OTHER PUBLICATIONS

Ghadieh et al., Chlorogenic acid/chromium supplement rescues diet-induced insulin resistance and obesity in mice, 2015, Nutrition & Metabolism, 12:19, pp. 1-7.*

Yang et al. , Xylooligosaccharide supplementation alters gut bacteria in both healthy and prediabetic adults: a pilot study, 2015, Front Physiol, 6: 216, p. 1-11.*
2015 https://www.fda.gov/files/food/published/GRAS-Notice-000614---Chromium-polynicotinate.pdf.*
Molly et al., (1993) Development of a 5-step multi-chamber reactor as a simulation of the human intestinal microbial ecosystem, Applied Microbial Biotechnology, 39(2), 254-258.
Possemiers et al., (2004) PCR-DGGE-based quantification of stability of the microbial community in a simulator of the human intestinal microbial ecosystem. FEMS Microbiology Ecology, 49(3), May 24, 2004, 495-507.
Van Den Abbeele et al., (2012) Incorporating a mucosal environment in a dynamic gut model results in a more representative colonization by lactobacilli, Microb Biotechnol, 5(1), 106-115.
Van De Wiele et al., (2004) Prebiotic effects of chicory inulin in the simulator of the human intestinal microbial ecosystem. FEMS Microbiology Ecology, 51(1), Aug. 21, 2004, 143-153.
De Weirdt et al., (2010) Human faecal microbiota display variable patterns of glycerol metabolism, FEMS Microbiology Ecology, 74(3), 601-611.
Vilchez-Vargas et al., (2013) Analysis of the microbial gene landscape and transcriptome for aromatic pollutants and alkane degradation using a novel internally calibrated microarray system, Environ Microbiol, 15(4), 1016.
Guo et al., (2008) Development of a real-time PCR method for Firmicutes and Bacteroidetes in faeces and its application to quantify intestinal population of obese and lean pigs. Lett Appl Microbiol, 47(5), 367-73.
Collado et al., (2007) Intestinal Integrity and Akkermansia muciniphila, a Mucin-Degrading Member of the Intestinal Microbiota Present in Infants, Adults, and the Elderly. Applied and Environmental Microbiology, 73(23), Sep. 30, 2007, 7767-7770.
Furet et al., (2009) Comparative assessment of human and farm animal faecal microbiota using real-time quantitative PCR. FEMS Microbiol Ecol, 68(3), 351-362.
Daguet et al., (2016) Arabinogalactan and fructooligosaccharides improve the gut barrier function in distinct areas of the colon in the Simulator of the Human Intestinal Microbial Ecosystem, Journal of Functional Foods 20, 369-379.

(Continued)

*Primary Examiner* — Terry A McKelvey
*Assistant Examiner* — Catheryne Chen
(74) *Attorney, Agent, or Firm* — Noblitt & Newson, PLLC

(57) ABSTRACT

Various embodiments of a gut microbiome modulating composition comprises a blend of a polyphenol and an oligosaccharide. Various embodiments of the polyphenol may comprise at least approximately 5% by weight chlorogenic acid. Various embodiments of the oligosaccharides may be standardized to a degree of polymerization of at least three to reduce digestibility. Administration of an effective amount of the gut microbiome modulating composition to a person or animal may stimulate the growth of at least one of *Akkermansia muciniphila, Lactobacillus,* and *Bifidobacterium* bacteria in the colon, which may reduce permeability of the colon, increases short chain fatty acid production in the colon, and/or modulate causes immunomodulation of human colon cells. The gut microbiome modulating composition may provide protective effects against obesity-related chronic diseases.

20 Claims, 16 Drawing Sheets

(56) References Cited

OTHER PUBLICATIONS

Rinttila et al., (2004) Development of an extensive set of 16S rDNA-targeted primers for quantification of pathogenic and indigenous bacteria in faecal samples by real-time PCR, Journal of Applied Microbiology 2004, 97, Jun. 19, 2004, 1166-1177.

Heilig et al., (2002) Molecular Diversity of *Lactobacillus* spp. and Other Lactic Acid Bacteria in the Human Intestine as Determined by Specific Amplification of 16S Ribosomal DNA. Applied and Environmental Microbiology, vol. 68. No. 1, Jan. 2002, 114-123.

Ovreas et al., (1997) Distribution of Bacterioplankton in Meromictic Lake Sælenvannet, as Determined by Denaturing Gradient Gel Electrophoresis of PCR-Amplified Gene Fragments Coding for 16S rRNA, Applied and Environmental Microbiology, vol. 63, No. 9, Sep. 1997, 3367-3373.

Van Den Abbeele et al., (2018) A combination of xylooligosaccharides and a polyphenol blend affect microbial composition and activity in the distal colon exerting immunomodulating properties on human cells, Vo. 47, Aug. 2018, 163-171.

\* cited by examiner

TEER (% of initial value) of Caco-2/THP1-Blue cocultures

IL-1β Cytokine Levels (pg/mL) on Caco-2/THP1-Blue co-cultures

CXCL10 Cytokine Levels (pg/mL) on Caco-2/THP1-Blue co-cultures

IL-10 Cytokine Levels (pg/mL) on Caco-2/THP1-Blue co-cultures

IL-8 Cytokine Levels (pg/mL) on Caco-2/THP1-Blue co-cultures

NF-κB activity (OD630) of THP1-Blue™ Cells

COMPOSITIONS AND METHODS FOR IMPROVING GUT HEALTH

CROSS-REFERENCES TO RELATED APPLICATIONS

This application claims the benefit of U.S. Provisional Application Ser. No. 62/502,571, filed May 5, 2017, and U.S. Provisional Application Ser. No. 62/513,135, filed May 31, 2017, incorporates the disclosures of each application by reference. To the extent that the present disclosure conflicts with the referenced applications, however, the present disclosure is to be given priority.

BACKGROUND

Obesity continues to be a major health epidemic across the globe. The majority of consumers are still heavier than medically recommended, and with worldwide obesity more than doubling since 1980, much of the world's population lives in countries where more deaths are caused by obesity than by being underweight, according to the World Health Organization (WHO). The Harvard T.H. Chan School of Public Health projected this rate to rise to around 50 percent by 2030. In the United States, nearly 73 percent of the population was classified as overweight (body mass index of between 25 and 30 kg/sq m) or obese (body mass index of more than 30 kg/sq m) in 2015—a figure that grew from 64% in 2005.

Excess weight is associated with many negative health outcomes, including higher incidences of diabetes, heart disease and cancer. In the United States, as in many other countries, obesity in particular is driving higher health care costs. According to research published by the University of Illinois in early 2015, obesity adds nearly US $1,400 to health care costs per person per year in the United States.

Accumulating evidence indicates that the gut microbiota plays a significant role in the development of obesity, obesity-associated inflammation, and insulin resistance, as well as metabolic disorders. The microbiota participate in host functions and impact the development and maintenance of the obese state, including host ingestive behavior, energy harvest, energy expenditure, and fat storage. In recent years, it has become apparent that alterations in gut microbiota composition is associated with the development of highly prevalent metabolic disorders in both animal and human studies. For example, there are consistent findings related to decreased abundance of *Akkermansia* in metabolic disorders in both preclinical and clinical studies. In contrast, the abundance of *Bifidobacterium* spp. and *Akkermansia muciniphila* were strongly associated with improved markers of lipid metabolism, negatively associated with inflammation in fat tissue, circulating glucose, triglycerides and insulin, and inversely correlated to body weight.

Consistent with altered gut microbiota in obese versus lean individuals, changes in gut microbial community composition are observed following weight loss. A decrease in the *Firmicutes/Bacteroidetes* ratio in obese individuals correlates with weight loss and suggests that modulating the abundance of specific bacterial communities might be beneficial in the treatment of obesity. Weight reduction may also improve gut microbial subpopulations involved in inflammatory processes. Nutritional manipulation of the composition and metabolic activity of the gut microbiota may be an important strategy to improve host health.

SUMMARY

Various embodiments of a gut microbiome modulating composition comprises a blend of a polyphenol and an oligosaccharide. Various embodiments of the polyphenol may comprise at least approximately 5% by weight chlorogenic acid. Various embodiments of the oligosaccharides may be standardized to a degree of polymerization of at least three to reduce digestibility. Administration of an effective amount of the gut microbiome modulating composition to a person or animal may stimulate the growth of at least one of *Akkermansia muciniphila, Lactobacillus,* and *Bifidobacterium* bacteria in the colon, which may reduce permeability of the colon, increases short chain fatty acid production in the colon, and/or modulate causes immunomodulation of human colon cells. The gut microbiome modulating composition may provide protective effects against obesity-related chronic diseases.

BRIEF DESCRIPTION OF THE DRAWING FIGURES

A more complete understanding of the present invention may be derived by referring to the detailed description when considered in connection with the following illustrative figures. In the following figures, like reference numbers refer to similar elements and steps throughout the figures.

Elements and steps in the figures are illustrated for simplicity and clarity and have not necessarily been rendered according to any particular sequence or scale. For example, steps that may be performed concurrently or in different order are illustrated in the figures to help to improve understanding of embodiments of the present invention.

The figures described are for illustration purposes only and are not intended to limit the scope of the present disclosure in any way. Various aspects of the present invention may be more fully understood from the detailed description and the accompanying drawing figures, wherein:

FIGS. 1A-C are graphical representations of short chain fatty acid production in the ascending, transverse, and descending colon, respectively, after treatment with an exemplary embodiment of the gut microbiome modulating composition;

Figure 5:
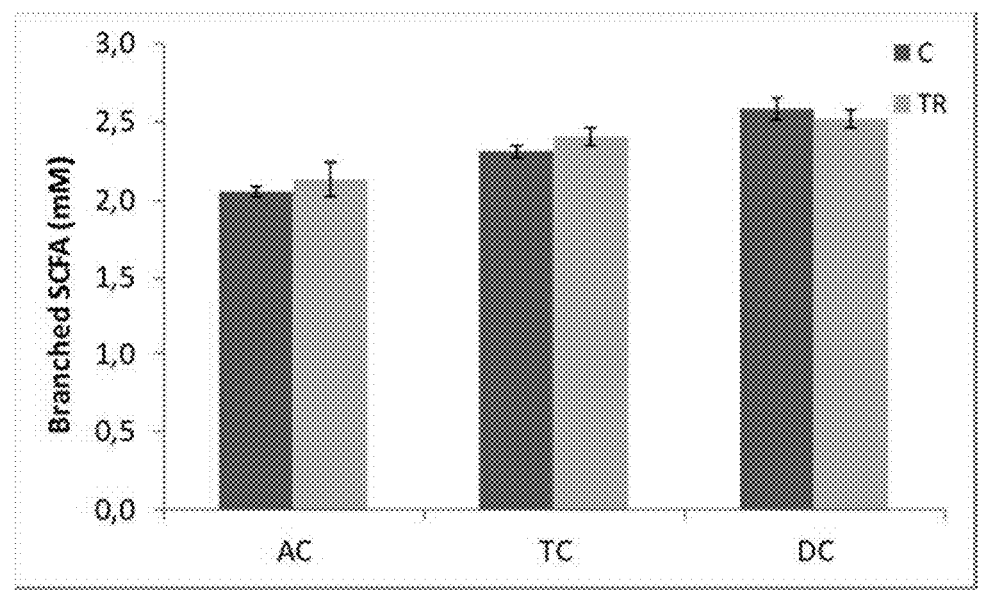
Figure 6:
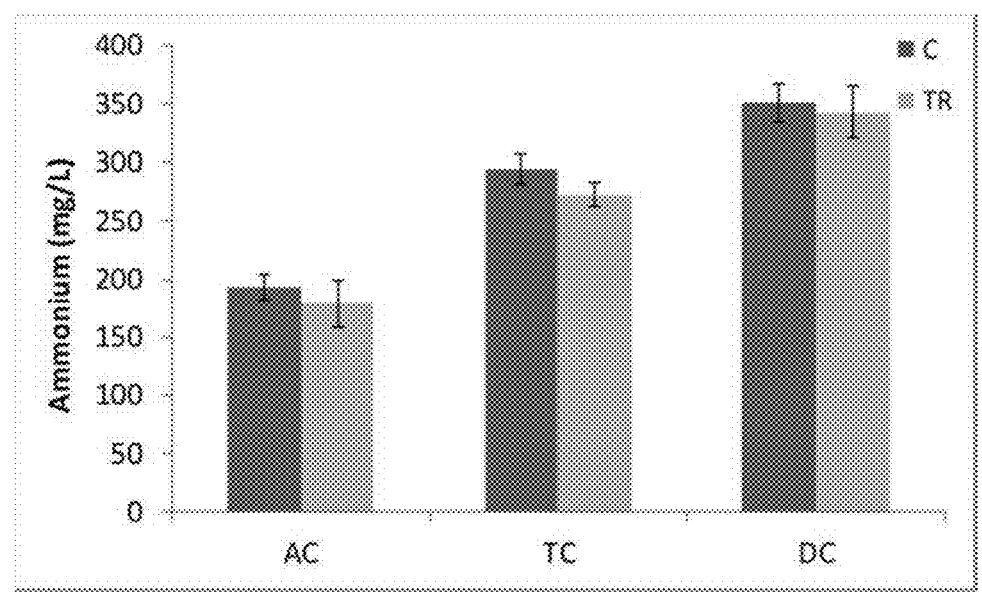
Figure 7:
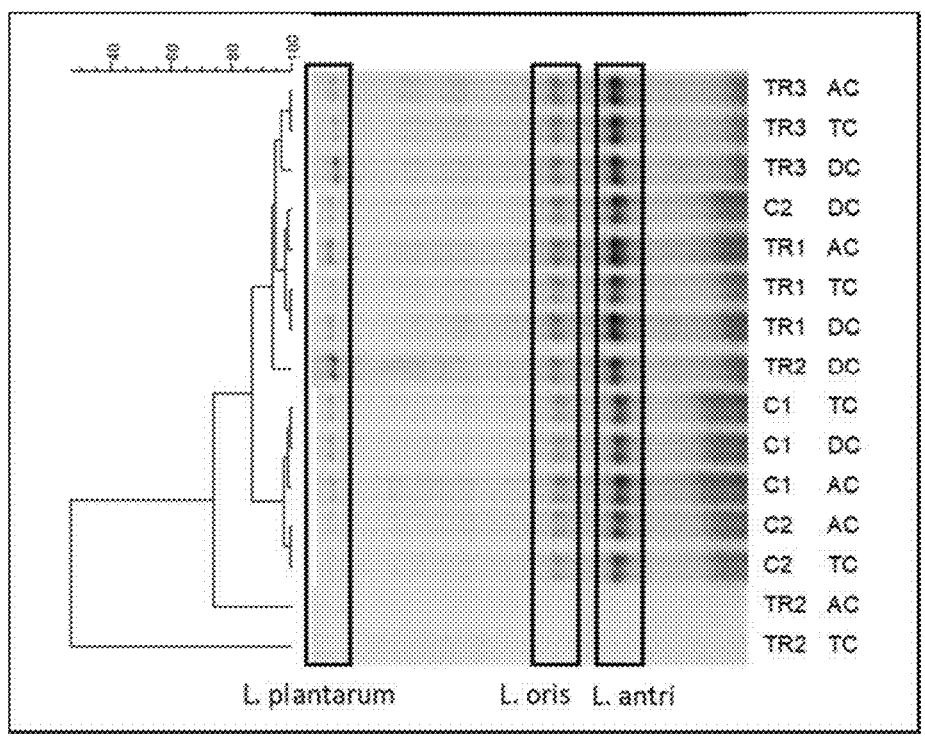

FIGS. 4A-H are graphical representations of measurements of the TEER of Caco-2 cells as a measure of gut barrier function (FIG. 4A) and cytokine levels in Caco-2/THP1-Blue co-cultures (Figures B-G) and NF-κB activity of THP1-Blue™ cells after treatment with samples collected from the ascending, transverse, and descending colon after treatment with an exemplary embodiment of the gut microbiome modulating composition;

FIG. 5 is a graphical representation of the branched SCFA produced in the ascending, transverse, and descending colon after treatment with an exemplary embodiment of the gut microbiome modulating composition;

FIG. 6 is a graphical representation of ammonium production in the ascending, transverse, and descending colon after treatment with an exemplary embodiment of the gut microbiome modulating composition; and FIG. 7 is a digital image of *Lactobacillus* DGGE profiles of the mucosal microbiota in the ascending, transverse, and descending colon.

DETAILED DESCRIPTION

The present invention may be described in terms of functional block components and various processing steps. Such functional blocks may be realized by any number of components configured to perform the specified functions and achieve the various results. For example, the present invention may employ various process steps, apparatus, systems, methods, materials, etc. In addition, the present invention may be practiced in conjunction with any number of methods for mixing ingredients and preparing ingredients for consumption, and the system described is merely one exemplary application for the invention.

The particular implementations shown and described are illustrative of the technology and its best mode and are not intended to otherwise limit the scope of the present technology in any way. For the sake of brevity, conventional manufacturing, preparation, process steps, and other functional aspects of the compositions may not be described in detail. Furthermore, connecting lines shown in various figures are intended to represent exemplary functional relationships and/or steps between the various elements. Many alternative or additional functional relationships or process steps may be present in a practical composition and method.

Various embodiments of the present technology provide compositions, methods, and systems for increasing healthy gut bacteria by ingesting food stuffs, beverages, and/or dietary supplements containing a gut microbiome modulating composition. The gut microbiome modulating composition may comprise efficacious amounts of a prebiotic and polyphenol blend that may increase the abundance of the bacterium *Akkermansia muciniphila*, as well as the abundance of *Lactobacilli* and *Bifidobacteria*, in the gut.

Conventional prebiotics often produce an undesired laxative affect and create gastrointestinal discomfort. This discomfort may particularly occur during the initial introduction of a prebiotic rich diet or dietary supplements containing efficacious levels of such prebiotics. This may lead consumers to stop consuming these products and sacrifice the benefit of the product to avoid the initial side-effects.

Various embodiments of the gut microbiome modulating composition may comprise one or more non-digestible prebiotics that exhibit minimal to no discernable gastrointestinal symptoms such as flatulence, discomfort, stool consistency, and/or defecation frequency. The prebiotic may beneficially affect the host person or animal by selectively stimulating the growth and/or the activity of particular bacteria in the distal colon. In various embodiments, the prebiotic may comprise non-digestible oligosaccharides (NDOs) having a high degree of polymerization that resists digestion and absorption in the human small intestine with complete or partial fermentation in the large intestine. NDOs are carbohydrates that aid in maintaining the regularity of colonic functions.

In various embodiments, the NDO in the gut microbiome modulating composition may comprise any suitable oligosaccharide with a high degree of polymerization. In some embodiments, the NDO may have a high degree of polymerization of at least 3, 4, and/or more polymerized monosaccharides. In some embodiment, the NDO may be a mixture oligosaccharides that has been enriched for oligosaccharides that have a high degree of polymerization of at least 3, 4, and/or more polymerized monosaccharides.

In various embodiments, the NDO in the gut microbiome modulating composition may comprise at least one of: xylooligosaccharides (XOS), fructooligosaccharides, galactooligosaccharides, isomaltooligosaccharides, soyoligosaccharides, transgalact000ligosaccharides, inulin, Pyrodextrins, polydextrose, beta glucans, and resistant starches. In some embodiments, the NDA may comprise XOS. XOS may exhibit beneficial biological effects, including cholesterol reduction, enhanced mineral absorption, and immunomodulation. XOS selectively stimulates growth of *Bifidobacterium* levels in the human gastrointestinal tract at consumption levels which are much lower than other widely used prebiotics.

Various embodiments of the gut microbiome modulating composition may comprise one or more polyphenols. In some embodiments, the polyphenol may be any plant or plant extract comprising chlorogenic acid. In some embodiments, the polyphenol may be at least 5% by weight chlorogenic acid. For example, the polyphenol may be at least 40% or 50% by weight chlorogenic acid. In some embodiments, the polyphenol may comprise at least one of: green coffee bean extract (GCBE), green tea, bamboo, heather shoots, hibiscus leaves, tea leaves, potatoes, eggplant flesh, peaches, prunes, and sunflower leaves. For example, the polyphenol may comprise a green coffee bean extract that may be approximately 65% by weight chlorogenic acid. Various sources of polyphenols may be processed, extracted, and/or concentrated using conventional methods to achieve the desired content of chlorogenic acid.

Polyphenols are secondary metabolites of plants that are involved in the defense against ultraviolet radiation or aggression by pathogens. Studies of polyphenols and phenolic acids have suggested that long term consumption of diets rich in plant polyphenols may reduce the incidence of cancers, cardiovascular diseases, diabetes, osteoporosis, and neurodegenerative diseases.

Coffee intake has protective effects against health conditions, such as type 2 diabetes, hypertension, liver dysfunction, and Parkinson disease. It has been suggested that these health benefits are due to coffee polyphenols, some of the main antioxidants in coffee. Chlorogenic acid is a main phenolic compound found in coffee and coffee beans. Chlorogenic acid levels are reduced by the process of roasting coffee beans. A cup of coffee typically contains 20 to 675 mg of chlorogenic acids, and the daily intake of chlorogenic acids by a coffee drinker is as much as 1 gram.

Chlorogenic acid has been implicated in weight loss, may reduce blood sugar levels, and potentially lower blood pressure. Animal studies documented that when supplementing with high-fat diet at 0.02% (wt/wt) dose, chlorogenic acid significantly lowered body weight, visceral fat mass and plasma leptin and insulin levels compared to the high-fat control group. They also lowered triglyceride (in plasma, liver and heart) and cholesterol (in plasma, adipose tissue and heart) concentrations. Chlorogenic acid suppressed high fat diet-induced increases in body weight and visceral fat-pad weight, serum lipid levels, and serum and hepatic free fatty acids in a dose-dependent manner. These results suggest that chlorogenic acid improve body weight, lipid metabolism and obesity-related hormones levels in high-fat fed mice.

Coffee is a relatively rich source of chlorogenic acids. As a considerable proportion of ingested chlorogenic acid reaches the large intestine and well utilized by the human fecal microbiota, chlorogenic acid may be capable of exerting beneficial effects in the large gut. The consumption of the coffee preparation resulting from water co-extraction of green and roasted coffee beans produce an increase in the metabolic activity and/or numbers of the *Bifidobacterium* spp. population, a bacterial group of reputed beneficial effects, without major impact on the dominant microbiota.

Plant parts rich in polyphenols like blueberries, grapes, tea leaves, and green coffee beans (coffee beans that have not been roasted), including green coffee bean extract (GCBE) have antioxidant properties and beneficial effects on gut health. The challenge associated with their use in consumer-friendly organoleptic products are the bitter alkaline flavors and astringency when used at efficacious levels. This challenge leads to very limited finished product offerings for the consumer and most polyphenol rich products are found in capsules or tablets which are meant to be swallowed and not tasted.

In various embodiments, the gut microbiome modulating composition may comprise a blend of prebiotic oligosaccharides and plant polyphenols. In some embodiments, the prebiotic oligosaccharide may be XOS and the polyphenol may be any suitable polyphenol comprising chlorogenic acid, such as GCBE. In some embodiments, the XOS may be standardized to high levels of long chain polymers and GCBE standardized to a minimum 50% chlorogenic acid. Both XOS and GCBE may be refined to increase solubility and/or to decrease unfavorable organoleptic attributes such as bitterness and/or astringency in taste.

In various embodiments, the gut microbiome modulating composition may contain an amount of XOS and GCBE effective to: (a) promote the growth of *Akkermansia muciniphila, Lactobacilli,* and/or *Bifidobacteria* in the colon, (b) promote immunomodulatory effects in the distal colon, (c) increase lactate levels in the ascending colon, (d) increase production of propionate and/or butyrate (SCFAs) in the colon, and/or (e) improve colon cell barrier function (i.e. reduce gut permeability).

In various embodiments, the ratio of XOS to GCBE in the gut microbiome modulating composition may be approximately 99:1 to approximately 50:50. In some embodiments, the ratio of XOS to GCBE may be from approximately 3:1 and approximately 2:1 by weight. In some embodiments, the effective amount of XOS per serving may be approximately 0.5 grams to 5 grams. For example, in one embodiment the amount of XOS per serving may be approximately 1 gram. In some embodiments, the effective amount of GCBE may be less than approximately 100 mg-1 grams. For example, the amount of GCBE in a serving may be approximately 400 mg. In various embodiments, approximately two servings per day of an exemplary embodiment of the gut microbiome modulating composition may be consumed by a person and/or animal to illicit the disclosed effects on the gut microbiome.

In some embodiments, the gut microbiome modulating composition may be formulated into an edible composition suitable for consumption by a human or animal. In various embodiments, the edible composition may comprise the gut microbiome modulating composition and a variety of additives. The additives may have any number of functions in the edible composition such as providing stability, increasing shelf-life, improving taste, protecting the gut microbiome modulating composition through at least part of the gastrointestinal tract, providing color, and any other desired physical, textural, and/or aesthetic characteristics. For example, the additives may comprise at least one of a preservative, a colorant (such as a fruit juice and/or a vegetable juice root extract), a fragrance, a pharmaceutical carrier, an excipient, a lubricating agent, a wetting agent, a sweetener (such as *Stevia rebuadiana* leaf extract), a flavorant, cellulose gum, and an excipient.

In some embodiments, the additive may comprise an ingredient with beneficial effects on health and/or metabolism. For example, the additive may comprise a chromium compound (such as chromium polynicotinate), fiber, vitamins, minerals, mulberry (alpha acid), garcinia cambogia extract, a citric acid, a fruit juice, a vegetable juice, an anti-caking agent such as silicone dioxide, and/or a filler.

In some embodiments, the gut microbiome modulating composition may be combined with an ingestible and/or pharmaceutically acceptable excipient that may act as a vehicle or medium. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose.

In some embodiments, the gut microbiome modulating composition may be formulated with lubricating agents such as talc, magnesium stearate, and mineral oil; wetting agents; emulsifying and suspending agents; preserving agents such as methyl- and propylhydroxy-benzoates; sweetening agents; and/or flavoring agents. The gut microbiome modulating composition may be formulated to provide a quick, sustained, or delayed release after administration to the person or animal by employing procedures known in the art.

In various embodiments, the gut microbiome modulating composition and/or the edible composition containing the gut microbiome modulating composition, may be enclosed in a carrier in the form of, for example, a capsule, tablet, paper, pills, powders, lozenges, sachets, cachets, elixirs, suspensions, emulsions, solutions, syrups, aerosols (as a solid or in a liquid medium), ointments, soft and hard gelatin capsules, suppositories, and/or sterile packaged powders. As is known in the art, the type of diluent can vary depending upon the intended route of administration.

Various embodiments of the gut microbiome modulating composition may be formulated into an ingestible form for administration to a person or animal. Exemplary embodiments of the gut microbiome modulating composition may be suitable for such administration in various food stuffs and dietary supplement formats, such as being added to a standard 16 oz water bottle, shaken and consumed as a beverage. This beverage may be consumed once or twice daily to improve gut health and also to aid in weight management by displacing other high calorie containing beverage options commonly found in the marketplace.

Testing Methodology and Results

To evaluate the effectiveness of exemplary embodiments of the gut microbiome modulating composition, a blend of XOS and GCBE plant extract blend rich in polyphenols, a validated in vitro gut model (i.e. SHIME®), coupled with co-cultures of epithelial cells and macrophages, was used to investigate the gut microbiome modulating composition's prebiotic potential and subsequent immune modulation of long-term administration within a colon. Overall, the results demonstrated that the gut microbiome modulating composition was well fermented along the entire colon leading to increased production of butyrate (+7 mmol/L) in the ascending colon (AC); acetate, propionate and butyrate (approx. +4 mmol/L each) in the transverse colon (TC); propionate (+4.1 mmol/L) in the descending colon (DC). The treatment led also to a mild decrease in ammonium and increased lactate levels in the AC, which correlated with an increase in luminal *Lactobacilli* and *Bifidobacteria* (+2.5 Log/mL). Additionally, the propionate-producing *Akkermansia muciniphila* increased in the lumen of the proximal colon (+2 Log/mL). Finally, a protective effect on Caco-2 barrier function was observed in the distal colon and pronounced immune activating properties (e.g. increase of NF-κB transcriptional activity) was found.

Materials and Methods
Chemicals and Test Product

All chemicals were obtained from Sigma-Aldrich (Overijse, Belgium) unless stated otherwise. Plexus Worldwide (Scottsdale, USA) provided an exemplary embodiment of the gut microbiome modulating composition (termed "Slim" in this study), which was tested at a dose of 1594 mg/day, containing 1000 mg of the prebiotic XOS and 250 mg of polyphenol mixture, containing green coffee extract (containing at least 50% chlorogenic acid), *Garcinia cambogia* fruit extract, alpha lipoic acid and Mulberry fruit extract.

Short-Term Colonic Incubation

Short-term colonic incubations were performed in penicillin bottles under anaerobic conditions (obtained by flushing with N2). Two different treatments (blank control and Slim) were evaluated for five different human donors (donor A, B, C, D and E). At the start of the colonic incubation, the test ingredients (0 mg or 1594 mg of Slim) were added to a sugar-depleted background medium, obtaining a final concentration of 0 g/L (blank control) or 2.66 g/L (Slim), respectively. Subsequently, fecal inocula were prepared for the different human volunteers by mixing a freshly collected fecal sample with anaerobic phosphate buffer ($K_2HPO_4$ 8.8 g/L; $KH_2PO_4$ 6.8 g/L; sodium thioglycolate 0.1 g/L; sodium dithionite 0.015 g/L) in a 1:5 (m:v) ratio. After homogenization (10 min, BagMixer® 400, Interscience, Louvain-La-Neuve, Belgium) and removal of big particles via centrifugation (2 min, 500 g), the fecal inoculum (1:10) was added to the different bottles. Incubations were performed during 48 h, at 37° C. and under continuous shaking (90 rpm). All experiments were performed in triplicate.

Simulator of the Human Intestinal Microbial Ecosystem (SHIME®)

The reactor setup was adapted from the SHIME® (ProDigest and Ghent University, Belgium), presenting the gastrointestinal tract of an adult human, as described by Molly, K. et al.[1] The SHIME® consists of a succession of five reactors simulating the different parts of the human gastrointestinal tract: stomach, small intestine and three colon regions. More specifically, the colon compartments simulate, upon inoculation with fecal microbiota from a healthy human volunteer (male, age 32), the ascending (AC), transverse (TC) and descending (DC) colon. Inoculum preparation, retention times, pH, temperature settings and reactor feed composition were previously described by Possemiers, S., et al.[2] For these experiments, the SHIME® setup was modified by incorporating a mucosal environment (so called M-SHIME®), which takes into account the colonization of the mucus layer, as reported by Van den Abbeele, P., et al.[3] The experimental setup of the SHIME run included a two-week start-up period, two-week control period and a three-week treatment period, as previously described by Van de Wiele, T., et al.[4]

[1] Molly, K., et al. (1993) Development of a 5-step multi-chamber reactor as a simulation of the human intestinal microbial ecosystem, *Applied Microbial Biotechnology*, 39(2), 254-258
[2] Possemiers, S., et al. (2004) PCR-DGGE-based quantification of stability of the microbial community in a simulator of the human intestinal microbial ecosystem. *FEMS Microbiology Ecology*, 49(3), 495-507.
[3] Van den Abbeele, P., et al. (2012) Incorporating a mucosal environment in a dynamic gut model results in a more representative colonization by lactobacilli. *Microb Biotechnol*, 5(1), 106-115.
[4] Van de Wiele, T., et al. (2004) Prebiotic effects of chicory inulin in the simulator of the human intestinal microbial ecosystem. *FEMS Microbiology Ecology*, 51(1), 143-153.

Microbial Metabolic Activity

For the short-term colonic incubations, pH (Senseline F410; ProSense, Oosterhout, The Netherlands), gas (handheld pressure indicator CPH6200; Wika, Echt, The Netherlands), SCFA and lactate measurements were performed after 0 h and 48 h of colonic incubation. During the SHIME® experiment, samples for microbial metabolic activity were collected three times per week during the control and treatment period. SCFA levels, including acetate, propionate, butyrate and branched SCFA (isobutyrate, isovalerate and isocaproate), were measured as described previously by De Weirdt, R., et al.[5] Lactate quantification was conducted using a commercially available enzymatic assay kit (R-Biopharm, Darmstadt, Germany) according to manufacturer's instructions. Ammonium analysis was performed as previously described by Van de Wiele, T., et al. (Id.) The effect of the treatment on pH was indirectly measured by calculating the difference in the amount of NaOH and HCl consumed to maintain the pH in the correct range in each colon vessel.

[5] De Weirdt, R., et al. (2010) Human faecal microbiota display variable patterns of glycerol metabolism. *FEMS Microbiology Ecology*, 74(3), 601-611.

Microbial Community Analysis

Samples for microbial community analysis were collected once per week during the control and treatment period from both the luminal and mucosal compartment of each colon vessel. Briefly, DNA was isolated using the protocol as described by Vilchez-Vargas, R., et al.[6], starting from 0.1 g mucosal sample or pelleted cells originating from 1 mL luminal sample. Subsequently, quantitative polymerase chain reaction (qPCR) for *Akkermansia muciniphila*, *Bacteroidetes* phylum, *Firmicutes* phylum, *Lactobacillus* spp. and *Bifidobacterium* spp. were performed on a StepOnePlus™Real-Time PCR system (Applied Biosystems, Foster City, Calif. USA). Each sample was analyzed in technical triplicate and outliers (more than 1 CT difference) were omitted. The qPCR for the *Firmicutes* and *Bacteroidetes* phyla were previously described by Guo, X., et al.[7], while the qPCR for *A. muciniphila* was performed as reported in Collado, M. C., et al.[8] The qPCR for *Lactobacillus* and *Bifidobacterium* spp. have been conducted as described by Furet, J. P., et al.[9] and Rinttilä, T., et al.[10], respectively.

[6] Vilchez-Vargas, R., et al. (2013) Analysis of the microbial gene landscape and transcriptome for aromatic pollutants and alkane degradation using a novel internally calibrated microarray system. *Environ Microbiol*, 15(4), 1016-1039.
[7] Guo, X., et al. (2008) Development of a real-time PCR method for *Firmicutes* and *Bacteroidetes* in faeces and its application to quantify intestinal population of obese and lean pigs. *Lett Appl Microbiol*, 47(5), 367-73.
[8] Collado, M. C., et al. (2007) Intestinal Integrity and *Akkermansia muciniphila*, a Mucin-Degrading Member of the Intestinal Microbiota Present in Infants, Adults, and the Elderly. Applied and Environmental Microbiology, 73(23), 7767-7770.
[9] Furet, J. P., et al. (2009) Comparative assessment of human and farm animal faecal microbiota using real-time quantitative PCR. *FEMS Microbiol Ecol*, 68(3), 351-362.
[10] Rinttild, T., et al. (2004) Development of an extensive set of 16S rDNA-targeted primers for quantification of pathogenic and indigenous bacteria in faecal samples by real-time PCR. *J Appl Microbiol*, 97(6), 1166-1177.

Denaturing Gradient Gel electrophoresis (DGGE) was used to separate the PCR products obtained with a nested approach for the 16S rRNA genes of *Lactobacillus* (primers GLAB0159f - SGLAB0667 (Heilig, H. G., et al.,[11] ). The first PCR round was followed by a second amplification with primers 338F-GC and 518R (Ovreas, L., et al.[12]. Subsequently, a clone library of the different PCR products was produced. Briefly, the obtained DNA sequences were purified (InnuPREP PCRpure Kit, AnalytikJena AG, Jena, Germany) and cloned into competent *E. coli* cells using the TOPO® TA Cloning Kit for Sequencing (Life Technologies, Carlsbad, USA), according to manufacturer's instructions. To make sure that all different DNA sequences in a sample were retained in the library, sufficient numbers of clones were collected from the culture plate. Upon collection of clones, the plasmid was extracted (InnuPREP Plasmid Rapid Kit, AnalytikJena AG) from the clones and the inserted DNA fragment was amplified (primer M13F and M13R). This fragment was sent for sequencing (LGC, Germany). Obtained DNA sequences were matched with specific sequence identity based on comparison with available databases (NCBI). Finally, DGGE fingerprinting was performed on the original samples and the clones, to link the bands in the DGGE gel with a species identity.

[11] Heilig, H. G., et al. (2002) Molecular diversity of *Lactobacillus* spp. and other lactic acid bacteria in the human intestine as determined by specific amplification of 16S ribosomal DNA. *Appl Environ Microbiol*, 68(1), 114-123.

[12] Ovreas, L., et al. (1997) Distribution of bacterioplankton in meromictic Lake Saelenvannet, as determined by denaturing gradient gel electrophoresis of PCR-amplified gene fragments coding for 16S rRNA. *Applied and Environmental Microbiology*, 63(9), 3367-3373.

Effects on Host Cells in Co-Culture Model of Epithelial Cells and Macrophages

The co-culture experiment was performed as previously described in Daguet, D., et al.[13] Briefly, Caco-2 cells (HTB-37; American Type Culture Collection, LGC Promochem, Molsheim, France) were seeded in 24-well semi-permeable inserts (0.4 μm pore size) at a density of $1 \times 10^5$ cells/insert. Caco-2 cell monolayers were cultured for 14 days, with three medium changes/week, until a functional cell monolayer with a Trans-epithelial electrical resistance (TEER) of more than 300 Ωcm$^2$ was obtained. Cells were maintained in Dulbecco's Modified Eagle Medium (DMEM) containing 25 mM glucose and 4 mM glutamine and supplemented with 10 mM HEPES and 20% (v/v) heat-inactivated (HI) fetal bovine serum (FBS). THP1-Blue™ (InvivoGen, Toulouse, France) cells were maintained in Roswell Park Memorial Institute (RPMI) 1640 medium containing 11 mM glucose and 2 mM glutamine and supplemented with 10 mM HEPES, 1 mM sodium pyruvate and 10% (v/v) HI-FBS. THP1-Blue™ cells were seeded in 24-well plates at a density of 5×105 cells/well and treated with 100 ng/mL of PMA for 48 hours to induce differentiation into macrophage-like cells.

[13] Daguet, D., et al. (2016) Arabinogalactan and fructooligosaccharides improve the gut barrier function in distinct areas of the colon in the Simulator of the Human Intestinal Microbial Ecosystem. *Journal of Functional Foods*, 20, 369-379.

Before co-culture, the TEER of the Caco-2 monolayers was measured by using an Epithelial Volt-Ohm meter (Millicell ERS-2; Millipore, Overij se, Belgium). The TEER of an empty insert was subtracted from all readings to account for the residual electrical resistance of an insert. Then, the Caco-2-bearing inserts were placed on top of the PMA-differentiated THP1-Blue™ cells for further experiments, as previously described in Daguet, D., et al. (Id.) Shortly, the apical compartment was filled with sterile-filtered (0.22 μm) colonic SHIME® suspensions (diluted 1:5 (v/v) in Caco-2 complete media). Cells were also treated apically with 12 mM sodium butyrate as positive control. The basolateral compartment was filled with Caco-2 complete media. Cells were also exposed to Caco-2 complete media in both chambers as control. Cells were treated for 24 h, after which the TEER was measured. After subtracting the TEER of the empty insert, all 24 h values were normalized to its own 0 h value (to account for the differences in initial TEER of the different inserts) and are presented as percentage of initial value. Then, the basolateral supernatant was discarded, and cells were stimulated basolaterally with Caco-2 complete media containing 500 ng/mL of ultrapure LPS (*Escherichia coli* K12, InvivoGen). Cells were also stimulated basolaterally with LPS and 1 μM hydrocortisone and media without LPS as controls. After 6 h of LPS stimulation the basolateral supernatant was collected for cytokines measurement (human IL-1β, IL-6, IL-8, IL-10, TNF-α and CXCL10 by Luminex® multiplex (Affymetrix-eBioscience)) and for assessing NF-κB activity by the QUANTI-Blue™ assay (InvivoGen), according to the manufacturers' instructions. All treatments were done in triplicate. Cells were incubated at 37° C. in a humidified atmosphere of air/CO2 (95:5, v/v).

Statistics

Comparison of normally distributed data of the different control and treatment weeks on microbial metabolic markers and microbial community parameters was performed with a student's T-test for pairwise comparisons. Differences were significant if p<0.05.

To evaluate the difference between the treatment and control samples on host endpoints, a two-way Anova with Sidak's multiple comparisons test was performed (significances are depicted with an asterisk (*)). (*), (), (*) and (****) represent statistically significant differences between the control and treatment period with p<0.05, p<0.01, p<0.001, p<0.0001, respectively. Statistics were performed using GraphPad Prism version 7.00 for Windows (GraphPad Software, San Diego, USA).

The obtained DGGE patterns were analysed using the GelCompar software v.6.6 (Applied Maths, Sint-Martens-Latem, Belgium). The dendrograms of the DGGE profiles were created based on the Pearson correlation coefficient using UPGMA linkages. Intensities of the different bands were extracted from the DGGE gels and plotted as relative proportions.

Results

Donor Selection

The fermentation profile of the test product was assessed for 5 different donors (Table 1). Metabolic markers were modulated in a similar way for each of the five donors, with an increase in production of gas, lactate and SCFA (among which acetate, propionate and butyrate) and a decrease in pH and the production of bSCFA. As the trends observed following the fermentation of the test product were similar in the different donors, donor D—with a high metabolic activity—was selected for the long-term SHIME experiment.

TABLE 1

Donor Selection

| Metabolic marker | Donor A | Donor B | Donor C | Donor D | Donor E |
|---|---|---|---|---|---|
| Acetate (mM) | +5.18 ± 0.97 | +6.43 ± 1.17 | +8.68 ± 0.48 | +11.70 ± 0.78 | +9.38 ± 1.01 |
| Propionate (mM) | +1.96 ± 0.29 | +6.49 ± 0.92 | +1.18 ± 0.76 | +5.38 ± 0.72 | +2.79 ± 0.50 |
| Butyrate (mM) | +2.29 ± 0.95 | +1.64 ± 0.30 | +3.12 ± 0.36 | +1.58 ± 0.11 | +2.35 ± 0.28 |
| Branched SCFA (mM) | −0.50 ± 0.09 | −0.62 ± 0.12 | −2.04 ± 1.03 | −1.05 ± 0.51 | −0.67 ± 0.22 |
| Total SCFA (mM) | +8.92 ± 1.89 | +13.94 ± 2.40 | +10.95 ± 1.63 | +17.62 ± 1.40 | +13.85 ± 1.45 |
| pH | −0.28 ± 0.07 | −0.39 ± 0.04 | −0.33 ± 0.06 | −0.40 ± 0.02 | −0.30 ± 0.05 |

TABLE 1-continued

| | Donor Selection | | | | |
|---|---|---|---|---|---|
| Metabolic marker | Donor A | Donor B | Donor C | Donor D | Donor E |
| Gas pressure (kPa) | +21.97 ± 1.19 | +14.93 ± 1.83 | +12.67 ± 1.37 | +17.23 ± 0.77 | +18.23 ± 2.20 |
| Lactate (mM) 0-6 h | +3.15 ± 0.14 | +2.01 ± 0.28 | +4.19 ± 1.15 | +3.22 ± 0.44 | +0.63 ± 0.25 |
| 6-48 h | −3.75 ± 0.53 | −2.25 ± 0.50 | −5.95 ± 0.32 | −3.87 ± 1.71 | −1.18 ± 0.62 |

Net effect of test product on different metabolic markers for the different donors based on values recorded at the end of the 48 h incubation.
A positive value (± stdev) indicates an increase in the metabolic marker production for treatment with test product versus the respective blank, while a negative value (± stdev) indicates a decrease in the metabolic marker production of test product versus the respective blank.

Analysis of the Microbial Metabolic Activity

Figure 1A:
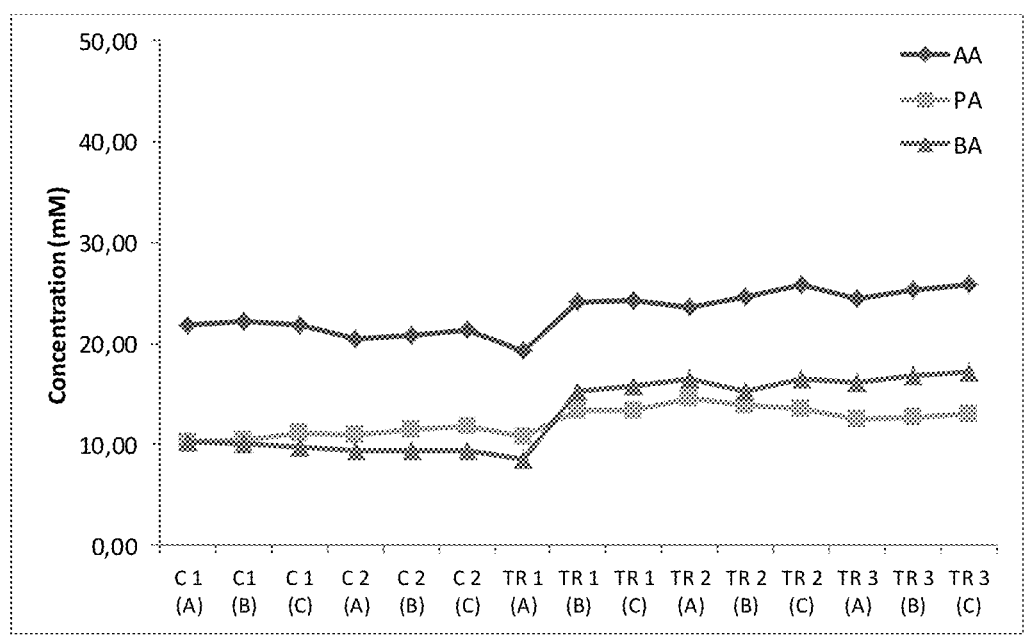
Figure 1B:
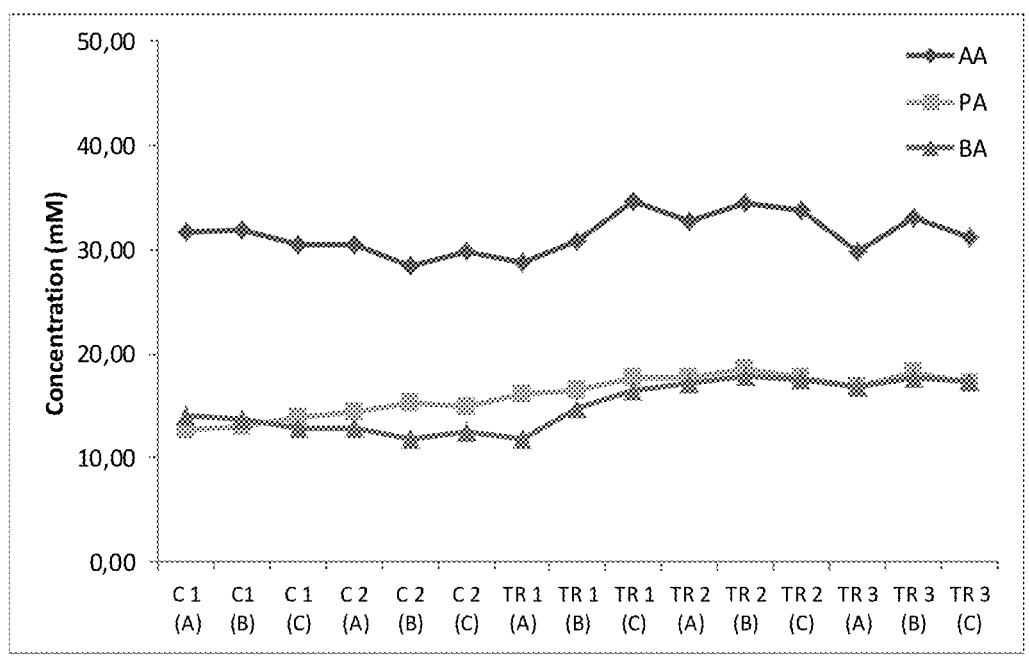
Figure 1C:
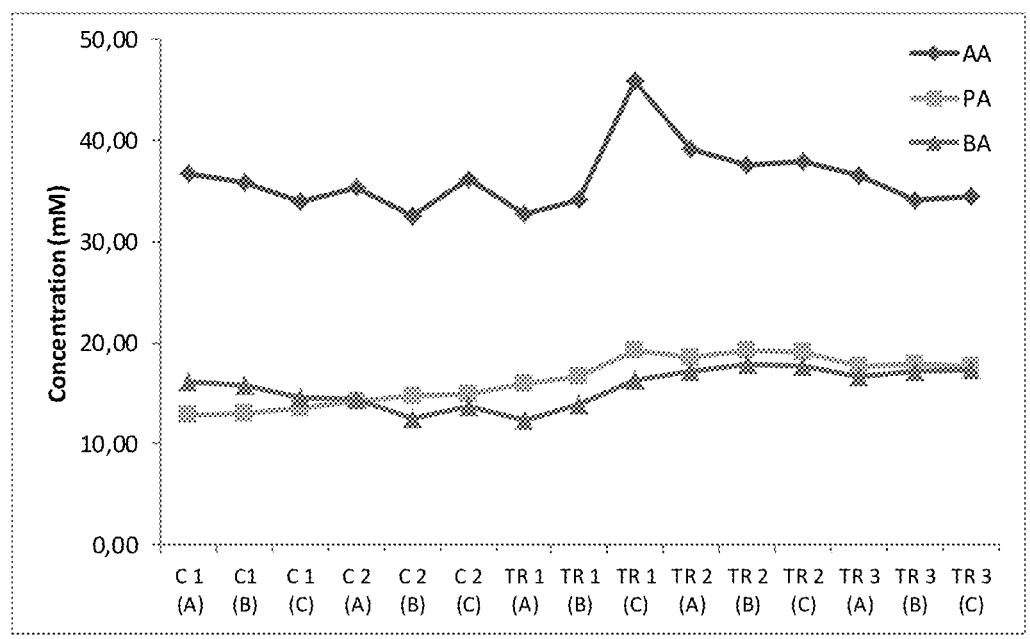
Figure 2:
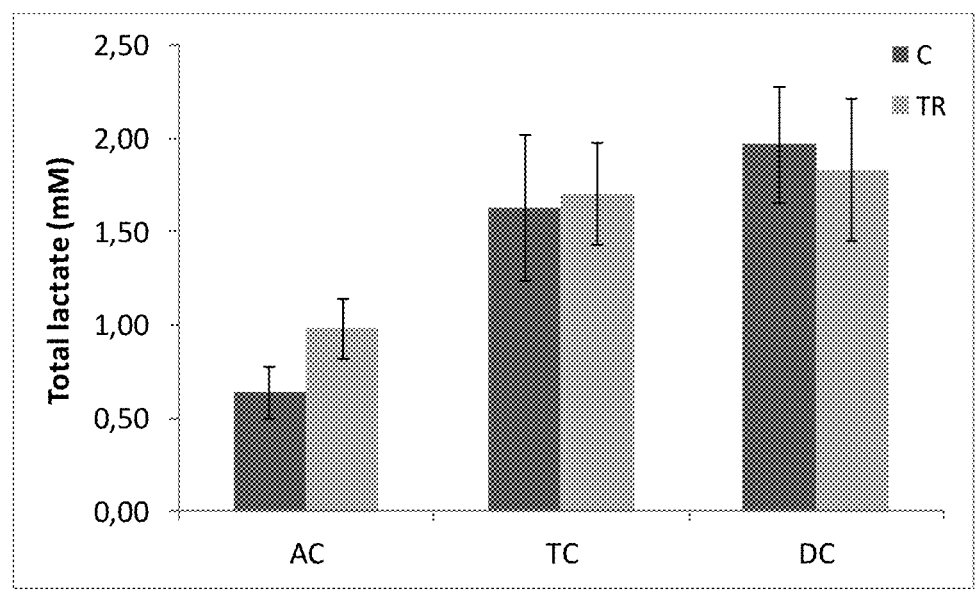
FIG. 2 is a graphical representation of lactate production in the ascending, transverse, and descending colon after treatment with an exemplary embodiment of the gut microbiome modulating composition.

The consumption of acid and base reflects the overall microbial activity throughout the experiment. Results showed an increased base consumption in AC, TC and DC upon the treatment, with 7.44 (±3.19), 4.86 (±4.17) and 1.98 (±1.38) mL/day respectively. This fermentation activity led to SCFA profiles which consisted mainly of acetate, propionate and butyrate (FIGS. 1A-C) and small amounts of branched SCFA (FIG. 5). More specifically, the test product led to an increased acetate production in all colon regions, with the effect being statistically significant in the ascending colon (p<0.01), i.e., an increase of 2.7 mM (+13%). Further, propionate increased in all three colon regions (p<0.001), i.e., 2.1 mM (+19%). 3.4 mM (+24%) and 4.1 mM (+30%) in AC, TC and DC respectively. Finally, butyrate production was significantly increased in AC and TC (p<0.01), with the butyrogenic effect being most pronounced in the AC (+7 mM (+84%)). Only a small effect was observed on branched SCFA levels during the treatment period. While a significant increase was observed in TC (+0.1 mM), slightly lower branched SCFA levels were observed in DC (−0.1 mM), although not statistically relevant (p=0.07). The treatment with the test product had a minor impact on ammonium (FIG. 6) and lactate (FIG. 2) production in the entire simulated colon. A significant accumulation of lactate was observed in the AC (+0.35 mM), whereas lactate levels remained unaffected in the TC and DC.

Analysis of the Microbial Community Composition

To assess the effect of the test product on specific taxonomic groups of interest (Bifidobacteria, Lactobacilli, Akkermansia muciniphila, Bacteroidetes and Firmicutes), qPCR analysis was performed for both luminal (Table 2) and mucosal (Table 3) microbiota. A first group under investigation was A. muciniphila. During the treatment, the levels of A. muciniphila increased in the luminal environment of the AC and TC (+2 log/mL, corresponding to a 257-fold increase in AC and +0.5 log/mL on average in TC). A gradual effect was observed in the AC, where levels increased especially during the second and third week of treatment, whereas a direct treatment effect was observed in the TC (+0.75 log (or +8%) during the first week of treatment).

TABLE 2

| Luminal microbial community composition as assessed via qPCR. | | | | | | |
|---|---|---|---|---|---|---|
| | | C1 | C2 | TR1 | TR2 | TR3 |
| Akkermansia muciniphila | AC | 4.50 ± 4.44 | 4.68 ± 3.27 | 4.91 ± 3.91 | 5.91* ± 0.05 | 7.15* ± 0.14 |
| | TC | 9.05 ± 0.01 | 9.05 ± 0.00 | 9.79* ± 0.00 | 9.54* ± 0.00 | 9.31* ± 0.03 |
| | DC | 9.35 ± 0.02 | 9.70* ± 0.02 | 9.35 ± 0.01 | 9.54* ± 0.01 | 9.59* ± 0.01 |
| Lactobacillus spp. | AC | 6.50 ± 0.01 | 6.75* ± 0.02 | 6.71* ± 0.01 | 8.67* ± 0.31 | 9.20* ± 0.09 |
| | TC | 6.78 ± 0.05 | 6.64 ± 0.00 | 7.14* ± 0.02 | 7.09* ± 0.01 | 7.13* ± 0.00 |
| | DC | 6.38 ± 0.03 | 7.03* ± 0.13 | 6.63* ± 0.03 | 6.71* ± 0.07 | 6.91* ± 0.02 |
| Bifidobacterium spp. | AC | 7.21 ± 0.01 | 7.52* ± 0.03 | 7.64* ± 0.00 | 8.83* ± 0.00 | 9.86* ± 0.01 |
| | TC | 8.13 ± 0.04 | 7.77* ± 0.00 | 8.53* ± 0.03 | 8.27* ± 0.02 | 8.16 ± 0.12 |
| | DC | 8.04 ± 0.04 | 8.17* ± 0.00 | 7.92 ± 0.03 | 8.03 ± 0.01 | 8.13 ± 0.04 |
| Bacteroidetes phylum | AC | 8.28 ± 0.43 | 8.89 ± 0.00 | 8.78 ± 0.01 | 10.21* ± 0.37 | 9.83* ± 0.02 |
| | TC | 8.99 ± 0.01 | 8.84 ± 0.08 | 9.60* ± 0.04 | 9.24* ± 0.00 | 8.86 ± 0.04 |
| | DC | 8.62 ± 0.01 | 8.97* ± 0.01 | 8.80* ± 0.01 | 8.79* ± 0.01 | 8.80* ± 0.00 |
| Firmicutes phylum | AC | 7.81 ± 0.02 | 8.12* ± 0.01 | 8.25* ± 0.03 | 9.46* ± 0.02 | 9.58* ± 0.02 |
| | TC | 8.23 ± 0.01 | 8.09* ± 0.02 | 9.11* ± 0.01 | 8.64* ± 0.06 | 8.14* ± 0.00 |
| | DC | 7.82 ± 0.03 | 8.30* ± 0.08 | 8.16* ± 0.04 | 8.24* ± 0.01 | 8.13* ± 0.02 |

Average Akkermansia muciniphila, Bacteroidetes, Firmicutes, Bifidobacterium and Lactobacillus levels (log10 16S rRNA copies/mL) in the luminal phase of the ascending (AC), transverse (TC) and descending (DC) colon compartment.
Samples were taken during two control (C1 and C2) and three treatment (TR1, TR2, and TR3) weeks. Data is presented as mean ± stdev.
*Indicates statistically significant differences relative to the first control week C1 (p < 0.05).

TABLE 3

| Mucosal microbial community composition as assessed via qPCR. | | | | | | |
|---|---|---|---|---|---|---|
| | | C1 | C2 | TR1 | TR2 | TR3 |
| Akkermansia muciniphila | AC | 5.67 ± 0.10 | 5.24 ± 0.00 | 6.96* ± 0.20 | 5.64 ± 0.01 | 6.10* ± 0.06 |
| | TC | 7.80 ± 0.01 | 7.06* ± 0.01 | 7.14* ± 0.01 | 7.21* ± 0.05 | 8.01 ± 0.10 |
| | DC | 8.13 ± 0.10 | 7.87 ± 0.02 | 7.71* ± 0.01 | 7.95 ± 0.02 | 7.93 ± 0.00 |

TABLE 3-continued

Mucosal microbial community composition as assessed via qPCR.

|  |  | C1 | C2 | TR1 | TR2 | TR3 |
|---|---|---|---|---|---|---|
| Lactobacillus spp. | AC | 6.62 ± 0.01 | 5.77* ± 0.01 | 7.17* ± 0.01 | 6.26* ± 0.02 | 7.00* ± 0.04 |
|  | TC | 5.65 ± 0.05 | 5.48 ± 0.17 | 5.63 ± 0.04 | 6.19* ± 0.01 | 6.40* ± 0.06 |
|  | DC | 5.39 ± 0.07 | 5.49 ± 0.00 | 5.65 ± 0.11 | 5.63* ± 0.01 | 5.60 ± 0.02 |
| Bifidobacterium spp. | AC | 7.19 ± 0.03 | 6.02* ± 0.05 | 7.61* ± 0.01 | 6.16* ± 0.03 | 6.90 ± 0.14 |
|  | TC | 7.24 ± 0.00 | 6.83* ± 0.08 | 6.43* ± 0.02 | 6.44* ± 0.02 | 6.81 ± 0.18 |
|  | DC | 7.06 ± 0.07 | 7.26 ± 0.04 | 6.90 ± 0.05 | 6.45* ± 0.03 | 6.90 ± 0.08 |
| Bacteroidetes phylum | AC | 7.43 ± 0.01 | 6.40* ± 0.02 | 7.94* ± 0.00 | 6.61* ± 0.10 | 7.51 ± 0.25 |
|  | TC | 7.38 ± 0.03 | 6.81* ± 0.01 | 6.95* ± 0.03 | 7.06* ± 0.02 | 7.71* ± 0.03 |
|  | DC | 7.05 ± 0.03 | 7.23* ± 0.01 | 7.06 ± 0.03 | 7.23* ± 0.02 | 7.30* ± 0.01 |
| Firmicutes phylum | AC | 7.53 ± 0.23 | 6.74* ± 0.01 | 8.08 ± 0.12 | 6.87 ± 0.04 | 6.89 ± 0.01 |
|  | TC | 7.79 ± 0.03 | 7.32* ± 0.01 | 7.48* ± 0.07 | 7.50* ± 0.01 | 7.79 ± 0.00 |
|  | DC | 7.44 ± | 7.61* ± | 7.48* ± | 7.48 ± | 7.50* ± |

Average *Akkermansia muciniphila*, Bacteroidetes, Firmicutes, *Bifidobacterium* and *Lactobacillus* levels (log10 16S rRNA copies/mL) in the mucosal phase of the ascending (AC), transverse (TC) and descending (DC) colon compartment.
Samples were taken during two control (C1 and C2) and three treatment (TR1, TR2 and TR3) weeks. Data is presented as mean ± stdev.
*Indicates statistically significant differences relative to the first control week C1 ($p < 0.05$).

Figure 3:
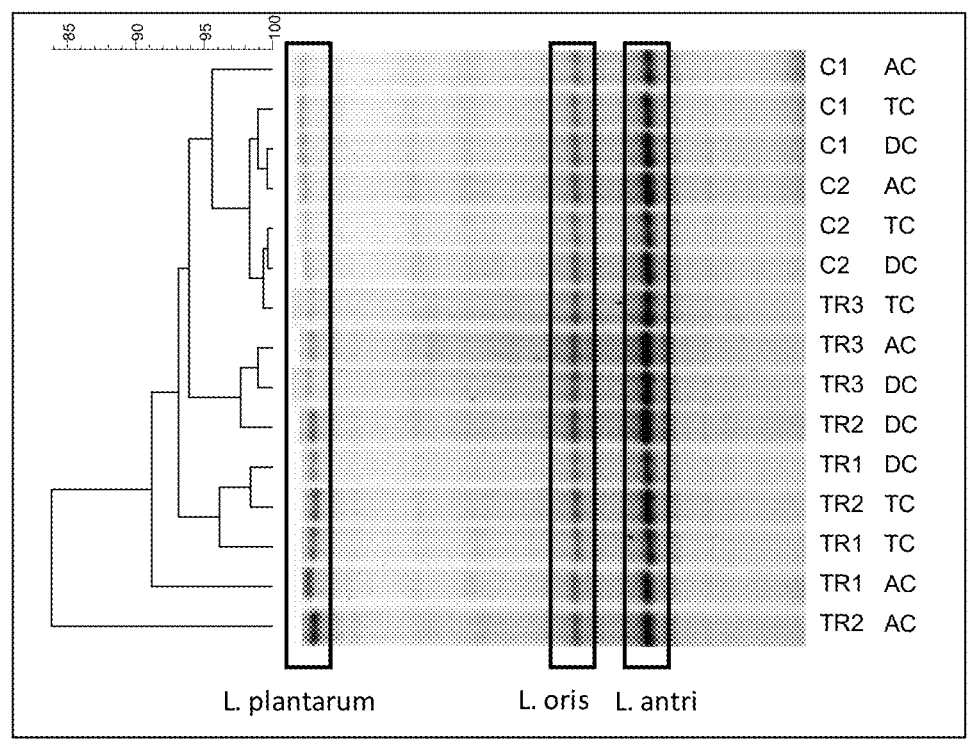
FIG. 3 is a digital image of *Lactobacillus* denaturing gradient gel electrophoresis (DGGE) profiles of the luminal microbiota in the ascending, transverse, and descending colon.
Figure 4A:
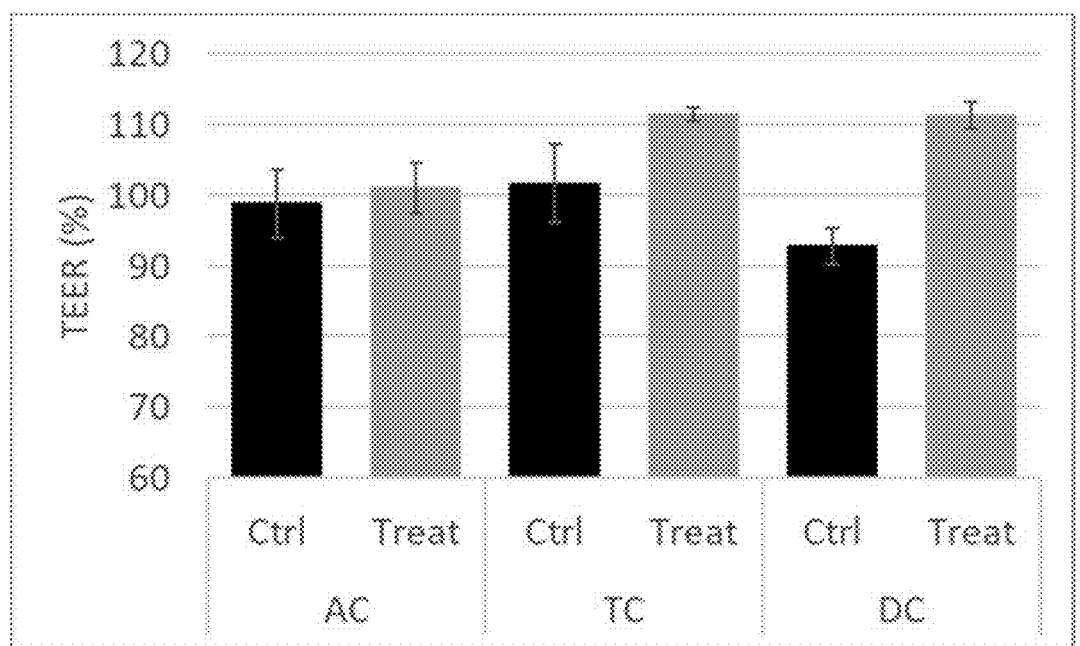
Figure 4B:
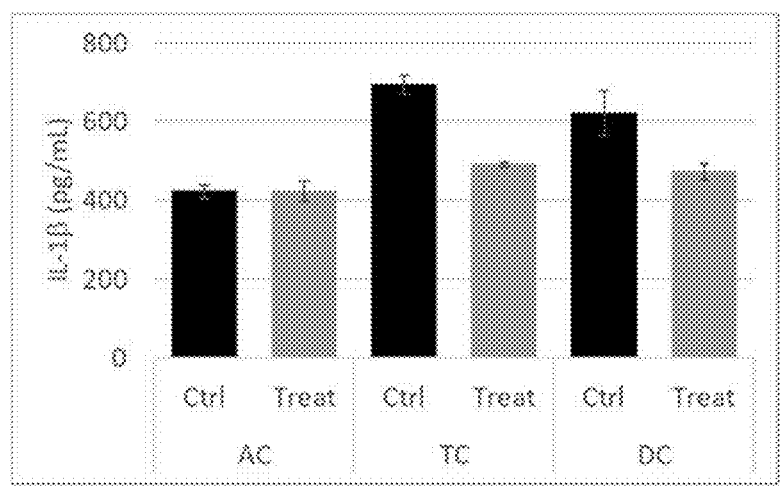
Figure 4C:
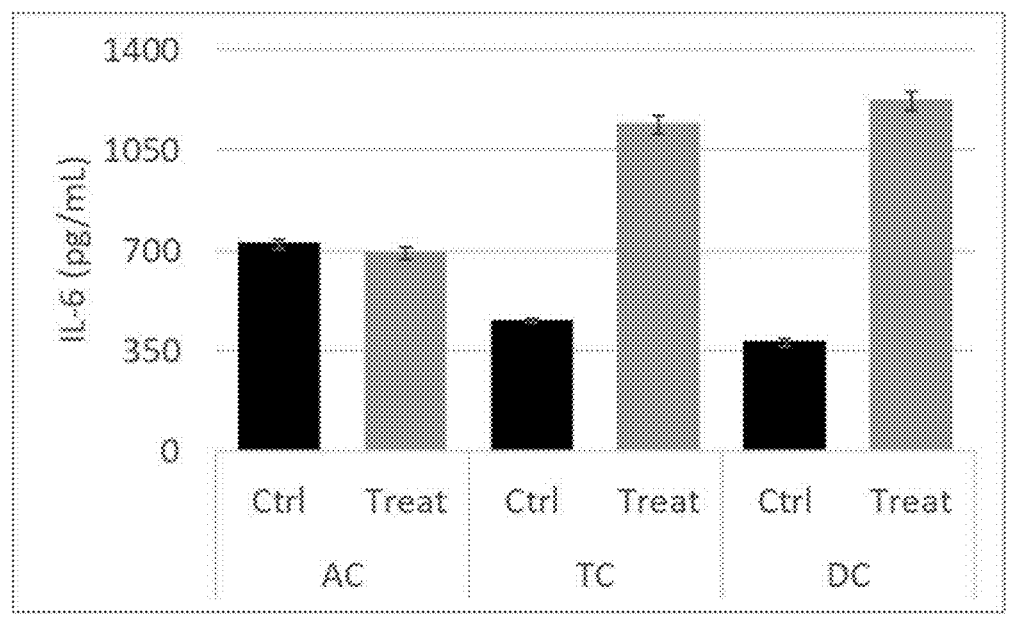
Figure 4D:
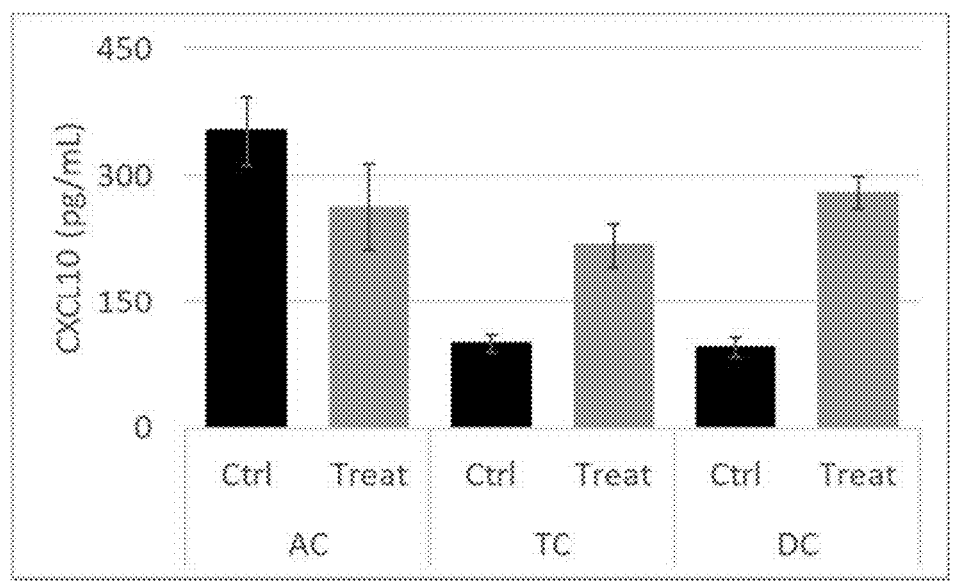
Figure 4E:
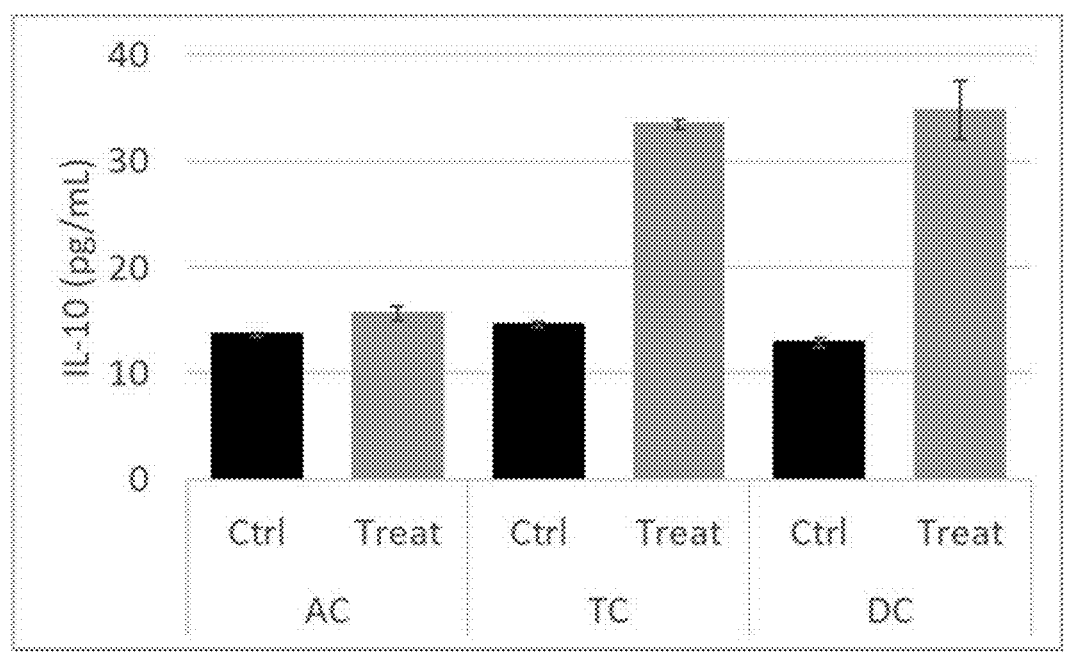
Figure 4F:
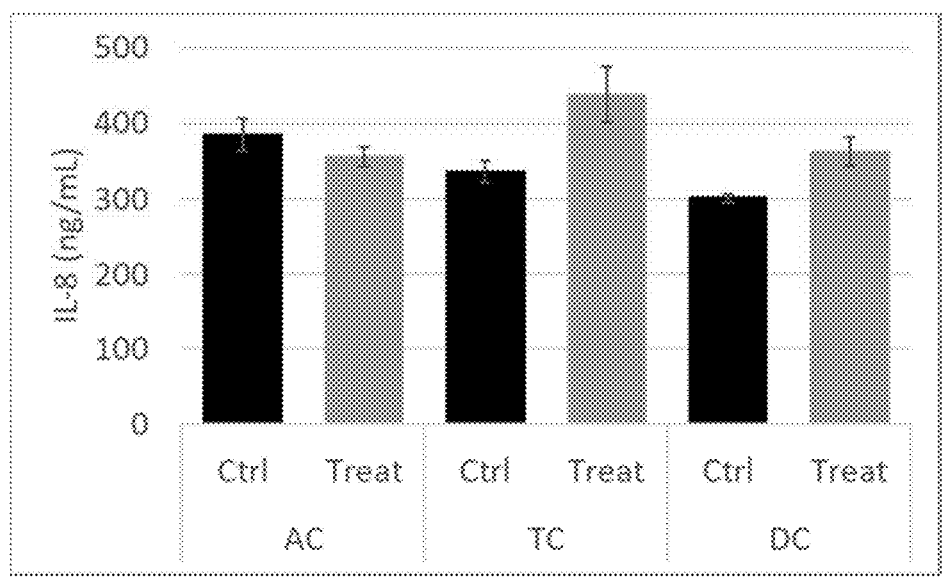
Figure 4G:
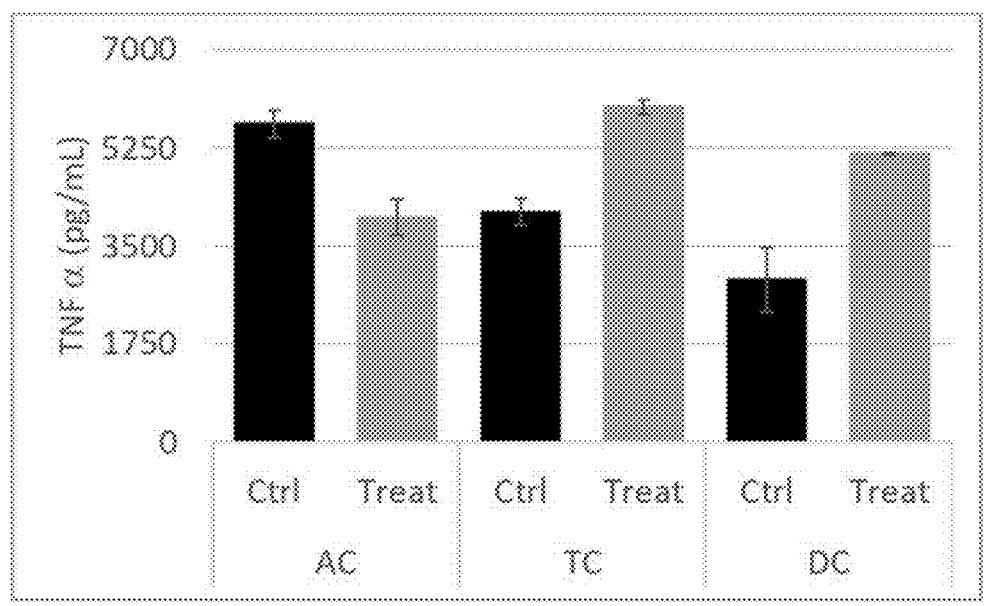
Figure 4H:
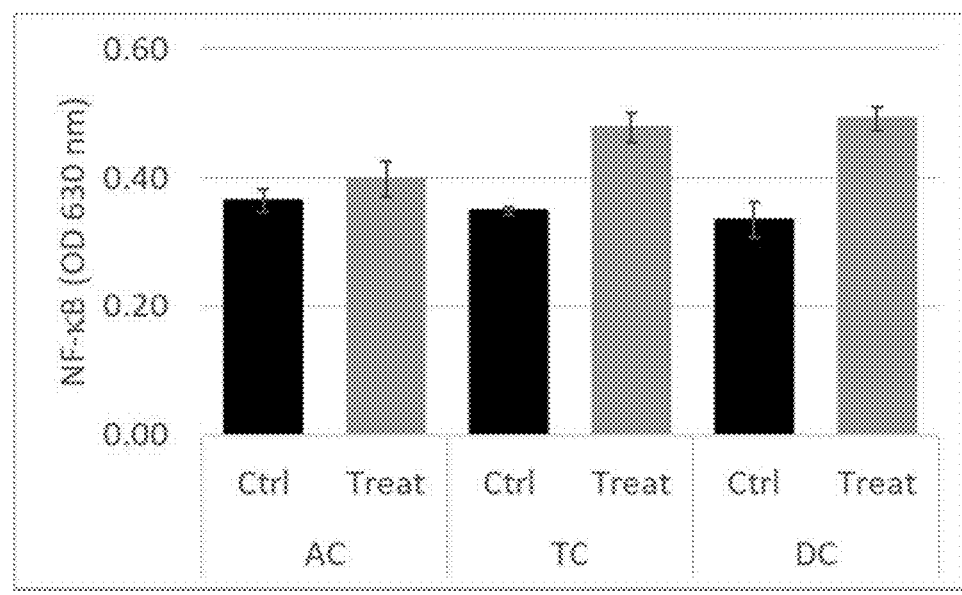

The *Firmicutes* and *Bacteroidetes* phyla were strongly increased in the luminal environment of the AC upon treatment with the test product, especially during the second and third week of treatment (at least +1.5 log/mL (+15%) for both phyla). Luminal *Firmicutes* and *Bacteroidetes* levels were not affected in the TC and DC. After an adaptation period, *Lactobacilli* and *Bifidobacteria* were stimulated in the lumen of the AC during the second and third week of treatment (more than +2.5 log/mL (>30%) for both genera). A luminal increase in *Lactobacillus* spp. levels was also observed in the TC, however less pronounced then in the AC (+0.4 log/mL). The luminal *Lactobacillus* community was mainly dominated by the operational taxonomic units (OTUs) related to three different species, i.e. *Lactobacillus plantarum*, *Lactobacillus oris* and *Lactobacillus antri* (FIG. 3). During the control period (C1 and C2) the relative abundance of these species was around 9-22%, 25-30% and 49-64% in the three colon regions for the three strains, respectively (Table 4). During the treatment period, the relative abundance of *Lactobacillus plantarum* tended to increase to 19-33% in the three colon regions.

TABLE 4

*Lactobacillus* abundance.

|  |  |  | C1 | C2 | TR1 | TR2 | TR3 |
|---|---|---|---|---|---|---|---|
| Lactobacillus antri | AC | Lumen | 56 | 58 | 44 | 56 | 54 |
|  |  | Mucus | 72 | 81 | 56 | 49 | 58 |
|  | TC | Lumen | 49 | 64 | 56 | 42 | 56 |
|  |  | Mucus | 73 | 70 | 70 | 39 | 69 |
|  | DC | Lumen | 62 | 59 | 52 | 50 | 52 |
|  |  | Mucus | 74 | 73 | 67 | 61 | 49 |
| Lactobacillus oris | AC | Lumen | 30 | 29 | 23 | 22 | 29 |
|  |  | Mucus | 19 | 13 | 28 | 41 | 35 |
|  | TC | Lumen | 29 | 25 | 24 | 31 | 25 |
|  |  | Mucus | 18 | 27 | 25 | 33 | 26 |
|  | DC | Lumen | 29 | 28 | 26 | 33 | 29 |
|  |  | Mucus | 16 | 19 | 25 | 18 | 30 |
| Lactobacillus plantarum | AC | Lumen | 15 | 13 | 33 | 23 | 17 |
|  |  | Mucus | 9 | 5 | 16 | 10 | 7 |
|  | TC | Lumen | 22 | 11 | 20 | 27 | 19 |
|  |  | Mucus | 9 | 3 | 4 | 28 | 5 |
|  | DC | Lumen | 9 | 13 | 22 | 17 | 19 |
|  |  | Mucus | 10 | 8 | 8 | 21 | 21 |

Relative abundance (%) of three *Lactobacillus* species/groups based on the *Lactobacillus* DGGE profiles of the luminal and mucosal microbiota during the control (C1 and C2) and treatment (TR1, TR2 and TR3) period in the ascending (AC), transverse (TC) and descending (DC) colon compartment.

In contrast to the luminal environment, the test product did not affect mucosal levels of any of the bacterial groups tested (*Bifidobacterium* spp., *Lactobacillus* spp., *A. muciniphila*, Bacteroidetes and Firmicutes). Similarly as the luminal community, *Lactobacillus plantarum*, *Lactobacillus oris* and *Lactobacillus antri* were the three dominant *Lactobacillus* spp. at mucosal level (FIG. 7). During the control period (C1 and C2), *Lactobacillus antri* was the dominating species with a relative abundance of at least 70% (Table 4). Upon the treatment with the test product, the relative abundance of *Lactobacillus plantarum* and *Lactobacillus oris* tended to increase to 16-28% and 30-41%, respectively, in the three colon regions.

Effects on Host Cells in Co-Culture Model of Epithelial Cells and Macrophages

To study the potential impact of the test product on the human host, fermentation-derived microbial metabolites were evaluated on a co-culture model between epithelial Caco-2 cells and THP-1 macrophages. Upon measuring the TEER of Caco-2 cells as a measure of gut barrier function (FIG. 4A), all samples were able to maintain TEER values near 100%.

Treatment with the test product tended to increase the TEER in the TC (+9.7%), with significant increases being noted in the DC (+18.5%).Further, LPS-induced NF-κB transcriptional activity of THP1 macrophages (FIG. 4H) was more pronounced after the treatment period in the TC and DC when compared to the respective controls (+1.4 fold in TC and +1.5 fold in DC).

With respect to cytokine levels (FIG. 4B-G), LPS-induced IL-10 and IL-6 were significantly increased after the treatment period in both TC and DC (i.e. IL-6, +2.5 fold in TC and +3.2 in DC; IL-10, +2.3 fold in TC and +2.7 in DC). When compared to the corresponding controls, The treatment with the test blend induced less IL-1□□ (in TC and DC) and more IL-8 (only significant in TC), and increased CXCL10 levels in the DC. Finally, regarding TNF-□□ concentrations, the obtained results were reactor-dependent. Whereas a decrease was observed in the AC, an increase was noted in the TC and DC comparatively to the control samples.

Discussion

By using a validated in vitro model, which takes into account the full complexity of the gastrointestinal tract, coupled with a co-culture model which mimics the host-microbiome interactions, we were able to study the intestinal fate of long-term administration of a test product, which contains an exemplary embodiment of the gut microbiome modulating composition comprising a blend of XOS and a polyphenol blend, termed Slim. It was shown that Slim modulates the metabolic activity and community composition of the colonic microbiota resulting in immune activating properties on human cells.

In vitro gut models depend on human faecal samples to obtain a representative microbial community. However, large differences in colonic microbiota exist between human individuals as different microbes can occupy a specific niche in different individuals (e.g. *Ruminococcus gnavus* or *A. muciniphila* for mucin degradation). As these differences may affect the microbial metabolism of dietary ingredients, inter-individual variability must be taken into account in in vitro studies. The inter-individual variation of the fermentation of the test product was assessed for 5 different human adults in short-term colonic incubations. As the fermentability was similar between the different donors, the long-term SHIME experiment was performed using the microbial community of a single donor, which is the preferred approach as compared to pooling of faecal samples. Pooling of faeces of different donors is nowadays still considered a good option in obtaining a representative microbiota that takes inter-individual variability into account. However, in the pooled sample, microbes that occupy a similar niche are brought together, creating competition and the development of a novel microbial community that is similar to the one of a single individual.

The test product was well fermented along the entire length of the colon, increasing the production of acetate, propionate and butyrate in all colon areas. In the AC, the increase was mainly due to butyrate production, while in the TC, the increase resulted from an increased level of all three main SCFA. Finally, in the DC, the increase resulted from increased propionate production. SCFA production originates from colonic carbohydrate fermentation, but also the microbial conversion of phenolic compounds has been shown to improve production of SCFA. As carbohydrate fermentation mainly takes place in the proximal colon, the observed butyrogenic effect in the AC will mainly be associated with the fermentation of XOS. Several studies have observed an increase in butyrate production upon XOS fermentation. Butyric acid is considered as the main energy source for the gut epithelium and has shown protective effects against inflammation and colon cancer development. In addition, butyrate can promote satiety and reduce oxidative stress. On the other hand, the colonic location of polyphenol fermentation is less well defined. However, microbial metabolism of polyphenols is mainly investigated in a distal colon environment, indicating that the observed propiogenic effect in the DC is probably linked with the fermentation of the polyphenol blend. Polyphenol-rich extracts of black tea and red wine/grape juice may stimulate a slight increase in propionate production in the transverse and descending colon compartments in vitro. The health promoting activity of propionate is related to the inhibition of lipid and cholesterol synthesis in the liver and positive effects on glycemic control. The increased production of health-promoting SCFA in the distal colon compartments (TC and DC) are of particular interest as most prebiotics are predominantly fermented in the proximal regions of the colon, due to local saccharolytic metabolism. In the distal colon, however, fermentation is mainly proteolytic, resulting in the formation of bSCFA and ammonia. Considering that proteolytic fermentation is associated with the formation of toxic by-products and that this colon region is must vulnerable to colonic diseases, there is great interest in finding new prebiotics with biological activity in the distal colon.

With respect to microbial community changes, the five taxonomic groups of interest (*Bifidobacteria, Lactobacilli, A. muciniphila, Bacteroidetes* and *Firmicutes*) increased in the luminal environment of the AC during the treatment period. Furthermore, *A. muciniphila* and *Lactobacillus* spp. levels also increased in the lumen of the TC upon supplementation of the test product. Specific community analysis showed that the treatment not only increased the absolute levels of *Lactobacilli,* but also modulated the proportional abundance of different *Lactobacillus* spp. within the community, mainly increasing the relative abundance of *Lactobacillus plantarum*. The latter has been shown to be associated with weight protection, as compared to several other *Lactobacillus* spp. *Lactobacilli* and *Bifidobacteria* are considered as health-beneficial saccharolytic bacteria. XOS has been shown to selectively stimulate *Bifidobacterium* spp. levels in the human gastrointestinal tract, whereas it was demonstrated that polyphenols stimulate the growth of both *Lactobacilli* and *Bifidobacteria*. Both groups are capable of producing high concentrations of lactate, which is an important metabolite in the human colon environment as it exerts strong antimicrobial effects, but also because it is the driver of a series of trophic interactions with other bacteria, resulting in the production of downstream metabolites such as butyrate.

In addition, the microbial community data confirmed a recent finding that *A. muciniphila* specifically colonizes the distal colon regions (TC and DC), while virtually being absent in the AC. As *A. muciniphila* is the main propionate producer in the distal colon and is shown to be increased upon polyphenol supplementation, the observed propiogenic effect can be explained by the stimulation of this specific microorganism. Furthermore, *A. muciniphila* has recently been shown to be capable of preventing adverse effects caused by high-fat diet-induced obesity, including fat-mass gain, adipose tissue inflammation and insulin resistance.

The beneficial effects observed in terms of gut microbial composition and activity resulted in immunomodulatory effects on human cells, which were most pronounced in the distal colon. A protective effect on Caco-2 barrier function was found in the TC, but especially in the DC, for which a significant increase in TEER was observed. Additionally, the polyphenol/prebiotic mixture was found to have pronounced immune activating properties in vitro, being able to increase the expression of several immune mediators. Immune-enhancing effects have been documented in literature for both XOS and polyphenolic compounds.

Consumption of XOS improves markers of immune function in both broiler chickens and healthy humans. Another study has shown that the pro-inflammatory effects induced by a high-fat diet in healthy subjects are reduced by consumption of XOS in combination with inulin, while XOS alone did not show any immunomodulatory effect in this population. On the other hand, it has been shown that dietary polyphenols exert anti-inflammatory activity. A study in a dextran sulphate sodium (DSS)-induced colitis model in mice showed significant suppression of IL-1β expression upon chlorogenic acid supplementation. In addition, protective effects on epithelial integrity have been documented for several polyphenols and polyphenol-rich extracts. This could indicate that the immunomodulatory properties of the test product are at least partly attributed to the presence of polyphenols and their metabolites.

Conclusions

From this study, it can be concluded that the combination of XOS and a polyphenol mixture, containing green coffee extract, positively affects the human gut microbiome activity and composition (leading to a possible synergistic stimulation not only of *Bifidobacterium* spp. but also of *Lactobacillus* spp. and *A. muciniphila*), resulting in immunomodulatory properties, especially in the distal colon where most of chronic diseases occur. Moreover, when compared with literature, the generated data support a possible role of the test product in protecting against obesity-related adverse effects. However, future research is warranted to clinically study the effect on high-fat diet-induced obesity.

In the foregoing description, the technology has been described with reference to specific exemplary embodiments. Various modifications and changes may be made, however, without departing from the scope of the present technology as set forth. The description and figures are to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the steps recited in any method or process embodiment may be executed in any appropriate order and are not limited to the explicit order presented in the specific examples. Additionally, the components and/or elements recited in any system embodiment may be combined in a variety of permutations to produce substantially the same result as the present technology and are accordingly not limited to the specific configuration recited in the specific examples.

Benefits, other advantages and solutions to problems have been described above with regard to particular embodiments. Any benefit, advantage, solution to problems or any element that may cause any particular benefit, advantage or solution to occur or to become more pronounced, however, is not to be construed as a critical, required or essential feature or component.

The terms "comprises", "comprising", or any variation thereof, are intended to reference a non-exclusive inclusion, such that a process, method, article, composition, system, or apparatus that comprises a list of elements does not include only those elements recited, but may also include other elements not expressly listed or inherent to such process, method, article, composition, system, or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

The present invention has been described above with reference to an exemplary embodiment. However, changes and modifications may be made to the exemplary embodiment without departing from the scope of the present technology. These and other changes or modifications are intended to be included within the scope of the present invention.

What is claimed is:

1. A gut microbiome modulating composition in the form of a capsule, a tablet, a pill, or a powder, the composition comprising:
    a polyphenol, wherein the polyphenol comprises at least 5% by weight chlorogenic acid;
    an oligosaccharide, wherein a green coffee bean extract comprises the polyphenol and the oligosaccharide is a xylooligosaccharide; and
    chromium polynicotinate.

2. The gut microbiome modulating composition of claim 1, wherein the polyphenol comprising at least 5% by weight chlorogenic acid is extracted from green coffee beans.

3. The gut microbiome modulating composition of claim 1, wherein the polyphenol comprises at least 65% by weight chlorogenic acid.

4. The gut microbiome modulating composition of claim 1, wherein the polyphenol comprises at least 40% by weight chlorogenic acid.

5. The gut microbiome modulating composition of claim 1, wherein the polyphenol comprises at least 50% by weight chlorogenic acid.

6. The gut microbiome modulating composition of claim 1, wherein the polyphenol comprising at least 5% by weight chlorogenic acid comprises green tea.

7. The gut microbiome modulating composition of claim 1, wherein consumption of an effective amount of the polyphenol and the oligosaccharide improves gut health by stimulating the growth of *Akkermansia muciniphila* in a colon.

8. The gut microbiome modulating composition of claim 7, wherein the effective amount is approximately 400 mg of green coffee bean extract comprising the polyphenol and the oligosaccharide is approximately 1 gram of xylooligosaccharide.

9. The gut microbiome modulating composition of claim 1, wherein the weight ratio of xylooligosaccharide to green coffee bean extract is in a range from 99:1 to 50:50.

10. The gut microbiome modulating composition of claim 1, wherein the weight ratio of xylooligosaccharide to green coffee bean extract is in a range from 3:1 to 2:1.

11. The gut microbiome modulating composition of claim 1, wherein an effective amount of the xylooligosaccharide is in a range from 0.5 grams to 5 grams per serving.

12. The gut microbiome modulating composition of claim 1, wherein the effective amount of the xylooligosaccharide is approximately 1 gram per serving.

13. The gut microbiome modulating composition of claim 1, wherein an effective amount of the green coffee bean extract comprising the polyphenol comprising least 50% by weight of the chlorogenic acid is in a range from 100 mg to 1 gram per serving.

14. The gut microbiome modulating composition of claim 1, wherein the effective amount of the green coffee bean extract comprising the polyphenol comprising least 50% by weight of the chlorogenic acid is approximately 400 mg per serving.

15. A gut microbiome modulating composition in the form of a capsule, a tablet, a pill, or a powder, the composition comprising:
    a green coffee bean extract comprising at least 50% by weight chlorogenic acid; and
    a xylooligosaccharide,
    wherein the green coffee bean extract is in an amount of at least 15% by weight of the composition and the xylooligosaccharide is in an amount of at least 60% by weight of the composition,
    wherein the weight ratio of xylooligosaccharide to green coffee bean extract is in a range from 3:1 to 2:1,
    wherein an effective amount of the composition improves gut health by stimulating growth of *Akkermansia muciniphila*.

16. The gut microbiome modulating composition of claim 15, further comprising an excipient.

17. The gut microbiome modulating composition of claim 15, further comprising a chromium compound.

18. The gut microbiome modulating composition of claim 15, wherein the chlorogenic acid is in an amount of at least 8% by weight of the composition.

19. A gut microbiome modulating composition comprising:
    chlorogenic acid in an amount of at least 8% by weight of the composition;
    xylooligosaccharide in an amount of at least 60% by weight of the composition; and
    chromium polynicotinate,
    wherein consumption of an effective amount of the composition improves gut health by stimulating the growth of Akkermansia muciniphila in a colon.

20. The gut microbiome modulating composition of claim 19, wherein the effective amount is approximately 400 mg of green coffee bean extract comprising the polyphenol and the oligosaccharide is approximately 1 gram of xylooligosaccharide.

* * * * *